United States Patent
Hung

(10) Patent No.: US 10,780,129 B2
(45) Date of Patent: Sep. 22, 2020

(54) USE OF MESENCHYMAL STEM CELLS IN TREATING OSTEOARTHRITIS

(71) Applicant: NATIONAL YANG-MING UNIVERSITY, Taipei (TW)

(72) Inventor: Shih-Chieh Hung, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 323 days.

(21) Appl. No.: 15/552,410

(22) PCT Filed: Feb. 22, 2016

(86) PCT No.: PCT/CN2016/074290
§ 371 (c)(1),
(2) Date: Aug. 21, 2017

(87) PCT Pub. No.: WO2016/131430
PCT Pub. Date: Aug. 25, 2016

(65) Prior Publication Data
US 2018/0042966 A1   Feb. 15, 2018

Related U.S. Application Data

(60) Provisional application No. 62/118,827, filed on Feb. 20, 2015.

(51) Int. Cl.
| | | |
|---|---|---|
| *A61K 35/28* | (2015.01) | |
| *C12N 5/0775* | (2010.01) | |
| *A61L 27/20* | (2006.01) | |
| *A61L 27/38* | (2006.01) | |
| *A61K 9/00* | (2006.01) | |
| *A61K 47/34* | (2017.01) | |
| *A61K 47/36* | (2006.01) | |
| *A61K 35/12* | (2015.01) | |

(52) U.S. Cl.
CPC ............ *A61K 35/28* (2013.01); *A61K 9/0019* (2013.01); *A61K 47/34* (2013.01); *A61K 47/36* (2013.01); *A61L 27/20* (2013.01); *A61L 27/3834* (2013.01); *C12N 5/0663* (2013.01); *A61K 2035/124* (2013.01); *A61L 2400/06* (2013.01); *A61L 2430/06* (2013.01); *A61L 2430/10* (2013.01); *C12N 2500/02* (2013.01)

(58) Field of Classification Search
None
See application file for complete search history.

(56) References Cited

U.S. PATENT DOCUMENTS

2011/0070281 A1   3/2011   Altman et al.

FOREIGN PATENT DOCUMENTS

WO   WO 2014/035215 A1   3/2014

OTHER PUBLICATIONS

International Search Report, issued in PCT/CN2016/074230, dated May 9, 2016.
Written Opinion of the International Searching Authority, issued in PCT/CN2016/074290, dated May 9, 2016.

*Primary Examiner* — Blaine Lankford
(74) *Attorney, Agent, or Firm* — Birch, Stewart, Kolasch & Birch, LLP

(57) ABSTRACT

The present invention relates to a use of hypoxia-cultured mesenchymal stem cells (MSCs) for manufacture of a cell graft for treating a musculoskeletal disorder, particularly osteoarthritis.

11 Claims, 8 Drawing Sheets

Figure 4 - continued

USE OF MESENCHYMAL STEM CELLS IN TREATING OSTEOARTHRITIS

CROSS REFERENCE TO RELATED APPLICATIONS

This application is the National Phase of PCT International Application No. PCT/CN2016/074290, filed on Feb. 22, 2016, which claims priority under 35 U.S.C. 119(e) to U.S. Provisional Application No. 62/118,827, filed on Feb. 20, 2015, all of which are hereby expressly incorporated by reference into the present application.

FIELD OF THE INVENTION

The present invention generally relates to a new use of hypoxia-cultured mesenchymal stem cells for manufacture of a cell graft for treating a musculoskeletal disorder. In particular, the musculoskeletal disease is osteoarthritis.

BACKGROUND OF THE INVENTION

Osteoarthritis (OA) is an increasingly common joint disease in many countries. It is commonly known that OA can be treated with some anti-inflammatory drugs, analgesics, or lubricating supplements. Alternatively, OA can also be treated with a surgery including drilling, microfracture and mosacplasty for repair or reconstruction of the lesions, which only transiently improves the symptoms but does not provide permanent cure or regeneration of the degenerative tissues.

Hyaluronic acid (HA) was reported to be used in treatment of OA. Although the intra-articular injection of HA was used for treatment of OA, the effects of HA in chondro protection and the prevention of OA progression of the knee remained controversial. It was stated in some studies that the therapeutic effect of HA was not recognized in treatment of OA; and HA provided lubrication effect only (Lo et al., Intra-articular hyaluronic acid in treatment of knee osteoarthritis: a meta-analysis. JAMA 2003; 290:3115-21). Since HA was reported to localize at the articular surface after intra-articular infusion, progenitor or stem cells delivered in HA were considered to be delivered to the articular surface.

Recently, a cell-based therapy, including implantation of cells or engineered cartilage, has been developed to aid in the repair of articular cartilage defects. It was reported that cartilage defects in the knee were successfully treated by the transplantation of autologous chondrocytes cultured under a monolayer culture condition (Brittberg et al., Treatment of deep cartilage defects in the knee with autologous chondrocyte transplantation. N. Engl. J. Med. 1994; 331:889-95).

It was also indicated in the recent reports that mesenchymal stem cells (MSCs), capable of self-renewal and differentiating into various mesenchymal tissues, emerged as a promising tool for clinical applications. For example, cell-based therapy for osteogenesis imperfecta and tissue engineering in cartilage and bone (Wei et al., Mesenchymal stem cells in regenerative medicine for musculoskeletal disorders: bench, bedside, and industry. Cell Transplant. 2014; 23:505-12). Allogeneic MSCs from healthy donors may serve as a "universal donor cell" in treating patients with musculoskeletal disorders. However, the MSCs are not intrinsically immunoprivileged and allogeneic MSCs were rejected in immunocompetent MHC-mismatched recipients (Eliopoulos et al., Allogeneic marrow stromal cells are immune rejected by MHC class I- and class II-mismatched recipient mice. Blood, 2005; 106:4057-65). MSCs cultured under hypoxic conditions, referred to as hypoxic MSCs, especially for long-term, decreased replicative senescence but increased the proliferation rate and differentiation potential, as compared to MSCs expanded under normoxic conditions, referred to as normoxic MSCs (Tsai et al., Hypoxia inhibits senescence and maintains mesenchymal stem cell properties through down-regulation of E2A-p21 by HIF-TWIST. Blood, 2011; 117:459-69). Hypoxic MSCs increased the migration and engraftment to distant sites following transplantation. Hypoxic MSCs also secreted more angiogenic cytokines and growth factors than normoxic MSCs (Hung et al., Angiogenic effects of human multipotent stromal cell conditioned medium activated the PI3K-Akt pathway in hypoxic endothelial cells to inhibit apoptosis, increase survival, and stimulate angiogenesis. Stem Cells, 2007; 25:2363-70), and the conditioned medium derived from hypoxic MSCs have been applied for preventing sudden arrhythmic death, stimulating wound healing and fracture healing in rodent animals. Recently, it was reported that hypoxic MSCs increased the ability to survive and engraft in allogeneic host tissues and ameliorate ischemic limb via resisting host immune-rejection (Huang et al., Hypoxic mesenchymal stem cells engraft and ameliorate limb ischaemia in allogeneic recipients. Cardiovasc. Res. 2014; 101:266-76). The hypoxic MSCs were also applied for bone repair and tendon healing in allogeneic recipients (Huang et al., Mesenchymal stem cells from a hypoxic culture improve and engraft Achilles tendon repair. Am. J. Sports Med. 2013; 41:1117-25). However, there is no way to expect other effects of hypoxic MSCs.

SUMMARY OF THE INVENTION

This invention is based on the unexpected finding that hypoxia-cultured mesenchymal stem cells (MSCs) are effective in treating musculoskeletal disorders, particularly osteoarthritis.

Accordingly, the present invention provides a use of MSCs for manufacture of a cell graft for treating a musculoskeletal disorder, particularly osteoarthritis.

In another aspect, the present invention provides a method for treating a musculoskeletal disorder comprising administering a subject in need thereof with a therapeutically effective amount of a cell graft made of MSCs.

In the invention, the musculoskeletal disorder is selected from the group consisting of sprains, strains and tears of ligaments, tendons, muscles and cartilage, tendonitis, tenosynovitis, fibromyalgia, osteoarthritis, rheumatoid arthritis, polymyalgia rheumatica, bursitis, acute and chronic back pain, osteoporosis, carpal tunnel syndrome, DeQuervains's disease, trigger finger, tennis elbow, rotator cuff, ganglion cysts, osteogenesis imperfecta, Duschennes, Hurler's and Hunter's syndromes and combination thereof. In a particular example of the invention, the musculoskeletal disorder is osteoarthritis.

In one particular example of the invention, the MSCs are hypoxia-cultured MSCs, which may be obtained by culturing auto- or allo-MSCs under low oxygen conditions less than 10% oxygen.

In one embodiment of the invention, the hypoxia-cultured MSCs are obtained by culturing auto- or allo-MSCs under low oxygen conditions ranging from 0% to 7% oxygen, preferably 1% to 3% oxygen, most preferably about 1% oxygen.

In one or more examples of the present invention, the composition comprising hypoxia-cultured MSCs is administered through direct implantation, intravenous injection, intramuscular injection, intraosseous injection, intraperitoneal injection, intradermal injection, subcutaneous injection, or intra-articular injection. In one particular example, the composition comprising hypoxia-cultured MSCs is administered through intra-articular injection or direct implantation.

BRIEF DESCRIPTION OF THE DRAWINGS

The foregoing summary, as well as the following detailed description of the invention, will be better understood when read in conjunction with the appended drawing. In the drawings:

FIG. 2A shows the result of adipogenic differentiation, wherein the micrographs showing Oil Red O staining after 21 days of the induction; bars=50 μm.

FIG. 2B shows the result of osteogenic differentiation, wherein the micrographs showing Alizarin Red S staining after 21 days of the induction; bars=100 μm. FIG. 2C shows the result of chondrogenic differentiation, wherein the micrographs showing Alcian blue staining of the pallet after 21 days of the induction; bars=1 mm.

FIG. 3B shows the result of India ink staining for articular surface of tibial plateaus (bird's-eye view).

FIG. 4A provides the photomicrographs showing the haematoxylin of femur condyles in different groups after 6 and 12 weeks of the treatment. FIG. 4B provides the eosin and Safranin-O staining of femur condyles in different groups after 6 and 12 weeks of the treatment. FIG. 4C provides the results of the quantitative analysis of safranin-O staining. Data are mean±standard deviation. *P<0.05.

FIG. 7A shows the microscopic appearance of femur condyles stained with type X collagen (Magnification, ×100) (Upper box, ×400). FIG. 7B shows the quantitative analysis of type X collagen. Data are presented in mean±standard deviation. *P<0.05.

FIG. 8A shows the efficiency of endocytosis of SPIO nanoparticles into the mesenchymal stem cells. FIGS. 8B, 8C and 8D provide the photomicrographs showing engraftment of injected MSCs into cartilage by Prussian blue and Safranin-O staining at femoral condyle (Magnification, ×100), and tibial plateau (Magnification, ×100) and meniscus (Magnification, ×50), respectively. The lower boxes in FIGS. 8B and 8C are the images in 200×, and FIG. 8D provides the image in 100×.

DESCRIPTION OF THE INVENTION

Figure 1:
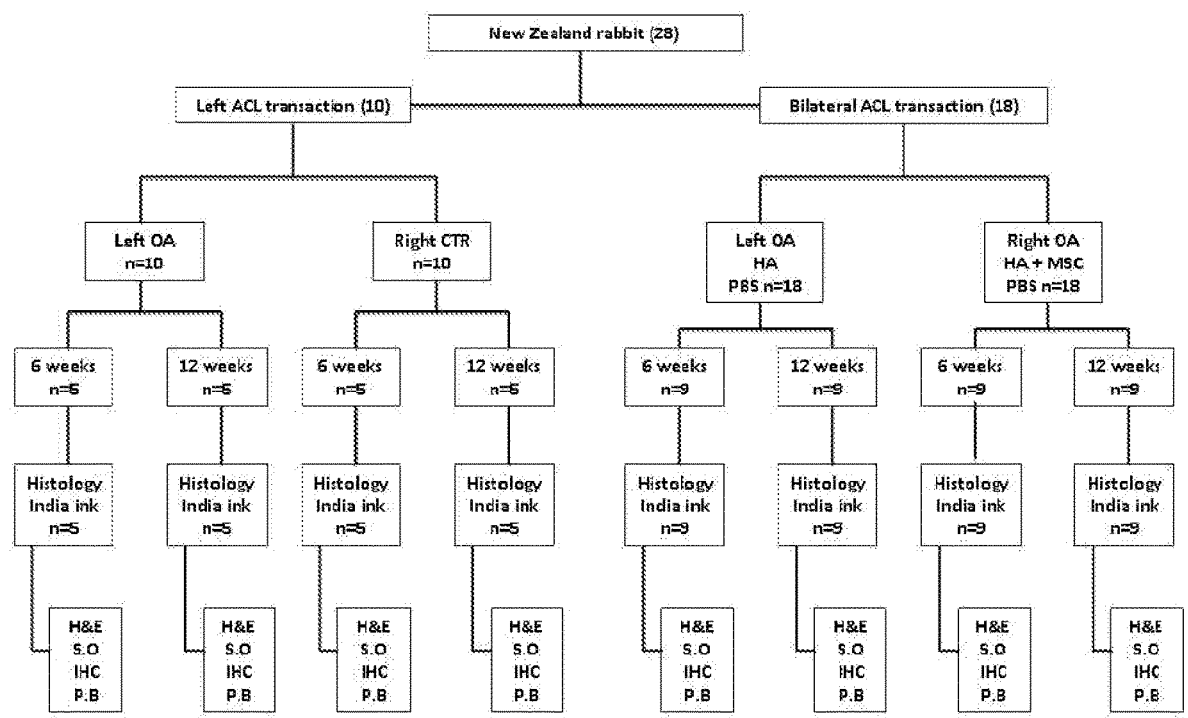
FIG. 1 shows the experiment design of the hypoxia-cultured MSCs for treating OAs in rabbits. The numbers in parentheses indicate number of rabbits receiving ACLT and analysis. (CTR: control group; H&E: haematoxylin and eosin; S.O: safranin O; P.B: Prussian blue)

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "musculoskeletal disorder" refers to an injury or pain in the body's bones, joints, ligaments, muscles, tendons, nerves, tendons, cartilages and structures that support limbs, neck and back, which is a degenerative disease and inflammatory condition that causes pain and impair normal activities. Examples of specific musculoskeletal disorders include all diseases related to bones, joints, ligaments, muscles, nerves, tendons, cartilages and structures that support limbs, neck and back. The musculoskeletal disorder is selected from the group consisting of sprains, strains and tears of ligaments, tendons, muscles and cartilage, tendonitis, tenosynovitis, fibromyalgia, osteoarthritis, rheumatoid arthritis, polymyalgia rheumatica, bursitis, acute and chronic back pain, osteoporosis, carpal tunnel syndrome, DeQuervains's disease, trigger finger, tennis elbow, rotator cuff, ganglion cysts, osteogenesis imperfecta, Duschennes, Hurler's and Hunter's syndromes and combination thereof.

As used herein, the term "mesenchymal stem cells" or "MSCs" refers to multipotent stem cells, which can differentiate into a variety of cell types, including for example, osteoblasts, chondrocytes and adipocytes etc. The mesenchymal stem cells or MSCs may be derived from any tissue sources, including but not limited to bone marrow tissues, adipose tissue, muscle tissue, corneal stroma or dental pulp of deciduous baby teeth, umbilical cord tissues or umbilical cord blood etc. In one example of the invention, the MSCs are bone marrow MSCs.

The term "hypoxia" as used herein refers to a condition of a lower oxygen content of air than normal oxygen content of atmosphere (e.g., 20%-25%), such as less than 10% oxygen.

The term "therapeutically effective amount" or "effective amount" refers to a predetermined amount calculated to achieve the desired effect, i.e., to prevention or treatment. The present invention provides a use of MSCs for manufacture of a cell graft for treating a musculoskeletal disorder, particularly osteoarthritis. On the other hand, the present invention also provides a method for treating osteoarthritis, comprises administering a subject in need thereof a therapeutically effective amount of a cell graft made of MSCs.

In the present invention, The MSCs are hypoxia-cultured MSCs, which may be auto- or allo-MSCs. The hypoxia-cultured MSCs are obtained by culturing auto- or allo-MSCs under low oxygen conditions less than 10% oxygen. In one example of the invention, the MSCs are cultured under the oxygen content ranging from 0% to 7% oxygen, preferably 1% to 3% oxygen, most preferably about 1% oxygen. In one particular example of the invention, the MSCs are allo-MSCs cultured under 1% oxygen.

According to the invention, a cell graft is made of the hypoxia-cultured MSCs. In one example of the invention, the hypoxia-cultured MSCs are obtained by the method of the steps:

(a) preparing a mammalian cell suspension containing MSCs in culture medium;
(b) culturing the mammalian cell suspension under hypoxic condition with 0% to 7% $O_2$; preferably 1%-7% $O_2$; more preferably 1%-3% $O_2$, most preferably about 1% $O_2$, in culture dish;
(c) changing the medium and subculturing the cells under the above mentioned hypoxic condition for at least 1 passage, preferably 2 passages; and
(d) recovering the MSCs as obtained in the step of (c).

In one example, the MSCs are cultured under the hypoxic condition for about nine days or more.

For example, the cell graft may be administered through direct implantation, intravenous injection, intramuscular injection, intraosseous injection, intraperitoneal injection, intradermal injection, subcutaneous injection, or intra-articular injection.

In the invention, the cell graft is made of hypoxia-cultured MSCs, which may further comprise an injectable vehicle that is suitable for delivering the MSCs to the defects, which is selected from the group consisting of a bio-polymer, a biomimetic composite of nature polymers and a synthetic polymer. The biomimetic composite of nature polymers may be hyaluronic acid, collagen, fibronectin, laminin, alginate, or chitosan etc. The synthetic polymer may be polythene (PE), such as low density polyethylene (LDPE) or high density polyethylene (HDPE), polypropylene (PP), polyvinyl chloride (PVC), polystyrene (PS), polytetrafluoroethylene (PTFE), polychlorotrifluoroethylene (PCTFE), polyacrylate, polyamide, polyester, polyurethane, polysulfide, polycarbonate having an element selected from the group consisting of oxygen, sulfur and nitrogen. In one or some examples of the invention, the injectable vehicle is collagen, fibrin glue or hyaluronic acid. In one particular example, the injectable vehicle is hyaluronic acid.

It is evidenced in the examples that osteoarthritis can be treated with the cell graft made of the hypoxia-cultured MSCs, which should be extended to other musculoskeletal disorders. Accordingly, the invention also provides a method for a musculoskeletal disorder, comprising administering a subject in need thereof with a therapeutically effective amount of a cell graft made of mesenchymal stem cells (MSCs). The musculoskeletal disorder is selected from the group consisting of sprains, strains and tears of ligaments, tendons, muscles and cartilage, tendonitis, tenosynovitis, fibromyalgia, osteoarthritis, rheumatoid arthritis, polymyalgia rheumatica, bursitis, acute and chronic back pain, osteoporosis, carpal tunnel syndrome, DeQuervains's disease, trigger finger, tennis elbow, rotator cuff, ganglion cysts, osteogenesis imperfecta, Duschennes, Hurler's and Hunter's syndromes and combination thereof.

The present invention is further illustrated by the following examples, which are provided for the purpose of demonstration rather than limitation.

Examples

1. Isolation of Rabbit Bone Marrow Mesenchymal Stem Cells

The protocol was approved according to the institutional animal welfare guidelines of Taipei Veterans General Hospital (Taipei, Taiwan). Both femora of 2 skeletally mature New Zealand white rabbits were removed, and the soft tissues were detached aseptically. Bone marrow was extruded by inserting an 18-gauge needle into the shaft of the bone and flushed out with basal medium ($\alpha$-minimal essential medium ($\alpha$-MEM), Gibco-BRL, Gaithersburg, Md.). Mononuclear cells were isolated from the bone marrow using density gradient centrifugation method, and were suspended in complete culture medium (CCM: $\alpha$-MEM supplemented with 16.6% fetal bovine serum, 100 U/mL penicillin, 100 µg/mL streptomycin, and 2 mM L-glutamine) and seeded in plastic dishes. After 24 hours of the initial culture, nonadherent cells were removed by changes of medium and irrigation of the culture. The culture typically reached 65% to 70% confluence within 6 to 8 days and reached subconfluence at Day 9, when the cells (passage 0) were harvested for further subcultures. Starting from passage 1, the cells were seeded at 100 cells/cm$^2$ and grown in CCM, wherein the medium was changed twice per week. For hypoxic cultures, the cells were cultured in a gas mixture composed of 94% $N_2$, 5% $CO_2$, and 1% $O_2$. For maintenance of the hypoxic gas mixture, an incubator with 2 air sensors, one for $CO_2$ and the other for $O_2$, was used; the $O_2$ content was achieved and maintained using delivery of $N_2$ gas from a tank containing pure $N_2$. $N_2$ gas was automatically injected into the system to displace the excess $O_2$ whenever the oxygen content rose above a desired level.

2. In Vitro Osteogenesis and Adipogenesis of MSC

MSCs were treated in one of the following culture conditions: (i) osteogenic differentiation medium of $\alpha$-MEM supplemented with 10% FBS, 50 g/ml ascorbate-2 phosphate (Nacalai, Kyoto, Japan), $10^{-8}$M dexamethasone (Sigma, St. Louis, Mo.) and 10 mM $\beta$-glycerophosphate (Sigma); and (ii) adipogenic differentiation medium of $\alpha$-MEM supplemented with 10% FBS, 50 µg/mL ascorbate-2 phosphate, $10^{-7}$M dexamethasone (Sigma), 50 µg/mL indomethacin (Sigma), 0.45 mM 3-isobutyl-1-methylxanthine (Sigma) and 10 µg/mL insulin (Sigma). Medium was changed every 3 days. After the appearance of morphologic features of differentiation, the cells were used for histochemical and immunofluorescence assay.

3. In Vitro Chondrogenesis of MSC

At semiconfluence, $5 \times 10^5$ MSCs were trypsinized and spun down at 500 g for 10 min. Within 12-24 hours of incubation, the cells formed an essentially spherical aggregate. The FBS-containing medium was replaced with chondrogenic medium consisting of serum-free high-glucose Dulbecco's modified Eagle's medium supplemented with ITS+Premix (BD Biosciences, Bedford, Mass.), 6.25 µg/ml insulin, 6.25 µg/ml transferrin, 6.25 µg/ml selenious acid, 1.25 mg/ml bovine serum albumin (BSA), 5.35 mg/ml linoleic acid), $10^{-7}$M dexamethasone (Sigma), 50 µg/ml ascobate-2-phosphate (Nacalai, Kyoto, Japan) and 10 ng/ml TGF-$\beta$1. Medium was changed at 2 to 3-day intervals and pellets were harvested at Day 21.

4. Cell Labeling with Superparamagnetic Iron Oxide Nanoparticles (SPIO)

The SPIO were prepared as described in Shieh (Shieh et al., Aqueous dispersions of magnetite nanoparticles with $NH^{3+}$ surfaces for magnetic manipulations of biomolecules and MRI contrast agents. *Biomaterials* 2005; 26:7183-91). In brief, 0.1 M Fe(III) (Sigma) and 0.2 M Fe(II) (Sigma) aqueous solution were prepared by dissolving $FeCl_3$ and $FeCl_2$, respectively. For production of $Fe_3O_4$ nanoparticles, 4 mL of Fe(III) and 1 mL of Fe(II) solutions were mixed at room temperature. Followed by adding 5 M NaOH, the pH of the mixed solution was adjusted dropwisely to 11. After collected by a magnet, the precipitates were washed with 50 mL of deionized water. Then, 3 g of organic acid was added to completely coat the particle surface. The precipitates were redispersed in deionized water after the removal of excess adherents by centrifugation. Before labeling, 50 µg/mL of SPIO were coated by mixing 0.75 µg/mL poly-L-lysine (Sigma) into the culture medium at room temperature for 1 hour to facilitate the endocytosis of SPIO nanoparticles. The MSCs were then seeded in 6-well plate at a density of $4 \times 10^4$/well and grown for 24 hours. The MSCs were incubated in SPIO-containing medium for 24 hours and washed with PBS thoroughly.

5. Osteoarthritis Model: ACLT (Anterior Cruciate Ligament Transection)

The knee joints of New Zealand Rabbits at 12 months of age and about 3.0 kg (ranging 2.8-3.5 kg) were divided into the following four groups (see FIG. 1): (1) OA (OA induction without HA nor MSCs treatment) (n=10), (2) contralateral control (sham operation); (3) OA with HA (HA treatment followed by OA induction) and (4) contralateral OA with HA plus MSCs (HA plus MSCs treatment followed by OA induction) (n=18). OA of knee joints were induced as described in Yoshioka (Yoshioka et al. Characterization of a model of osteoarthritis in the rabbit knee. *Osteoarthritis. Cartilage.* 1996; 4:87-98). In brief, a medial arthrotomy was performed. With the knee positioned in full flexion, the patella was dislocated laterally and the ACL (anterior cruciate ligament) was transected. The wounds were closed and covered with a local antibiotic ointment. All of the rabbits were returned to their cages after the operation and were allowed to move freely. OA was induced in the OA group (left knee), OA with HA group (left knee) and OA with HA plus MSCs group (right knee) by transection of ACL after 12 months. After 8 weeks after ACLT, the knee joints of the OA with HA group were injected with 0.4 ml (10 mg/mL) high molecular weight hyaluronic acid (HA) (Hya-Joint, SciVision Biotech, Taipei), while those of the OA with HA plus MSCs were injected with $10^6$ SPIO-labeled viable MSCs (passage 1) in 0.4 ml of HA. Half of the rabbits in each group were killed by 20 minutes of $CO_2$ inhalation after 6 weeks, and half were killed after 12 weeks after the HA or HA plus MSCs treatment.

6. Macroscopic Examination

The surface of distal femur and proximal tibia were exposed and examined macroscopically. Two (2) ml of India ink was injected onto the tibial plateau with a syringe. After 2 minutes, the surface was washed with saline. The staining pattern of the tibial plateau was examined macroscopically.

7. Histologic Analysis

For evaluation of differentiation potentials of these hypoxia-preconditioned cells, medium was removed from the culture, and cells were washed twice with PBS. The cells were fixed in 3.7% paraformaldehyde for 10 min. at room temperature and washed twice with PBS. The cells treated by osteogenic culturing were stained for alkaline phosphatase activity to reveal osteogenic differentiation. The cells treated by adipogenic and chondrogenic culture conditions were stained with oil red-O and alcian blue to show adipogenic and chondrogenic differentiation, respectively.

After rabbits were killed, the knees were harvested, and the femoral condyles with articular cartilage were collected and fixed with 10% neutral buffered formalin (Tonar Biotech; Taipei) prior to histologic preparation. The samples were then decalcified in 10% formic acid (Sigma)/PBS (Gibco/BRL, Grand Island, N.Y.). The decalcified femur articular samples were embedded in paraffin, and 4-µm microsections in the sagittal plane were prepared. Paraffin-embedded sections were stained with haematoxylin and eosin (HE). Glycosaminoglycan was stained with Safranin O fast green (1% Safranin O counterstained with 0.75% hematoxylin and then 1% fast green; Sigma), and the total and red-stained areas in the articular cartilage of each proximal tibia were measured by Image-Pro Plus software, version 5.0. The ratio of red-stained area to total area (red:total) in each group was calculated.

Prussian blue staining was performed to localize the iron particles in SPIO labeled MSCs or rabbit knee joints that received MSC treatment. For in vitro cell staining, the SPIO-labeled cells were washed twice with phosphate buffered saline (PBS) and fixed with 4% glutaraldehyde, then washed again and incubated for 30 min. with 2% potassium ferrocyanide in 6% hydrochloric acid. After washing 3 times with PBS, the iron content of cells were examined. For in vivo cell tracking, paraffin-embedded sections were deparaffinized and hydrated by distilled water. The sections were then immersed in equal parts of 12% hydrochloric acid and 4% potassium ferrocyanide (Sigma) for 30 min. Followed by washing the sections in distilled water for 3 times, the sections were counterstained with nuclear fast red for 5 minutes and rinsed twice in distilled water.

8. Immunohistochemistry Analysis

Localized type II collagen and type X collagen were immunostained. The femur articular sections were rehydrated, and the endogenous peroxidase in tissue was blocked with 3% hydrogen peroxide (Sigma). Type II collagen was retrieved with a mixture of 2.5% hyaluronidase (Sigma) and 1 mg/mL of Pronase in PBS (pH 7.4; Sigma) at 37° C. for 1 hour, while type X collagen was retrieved by treatment with 0.1 units/mL of chondroitinase ABC (Sigma) at 37° C. for 1 hour, followed by treatment with 1 mg/mL of pepsin (Sigma) in Tris HCl (pH 3.0, MDBio, Taipei, Taiwan) at 37° C. for 15 minutes. Sections were then blocked with Ultra V block (Thermo Scientific, Fremont, Calif.) for 10 min. and incubated with primary antibodies against type II collagen (mouse monoclonal antibody) (1:200; CP18; Calbiochem, La Jolla, Calif.) and type X collagen (rat polyclonal antibody) (1:200; ab58632; Abcam, Cambridge, Mass.) at 37° C. for 4 hours. The secondary antibodies were incubated for 30 min. using biotin-labeled goat anti-mouse immunoglobulin for type II collagen (Dako, Carpinteria, Calif.) and biotinlabeled goat anti-rabbit immunoglobulin for type X collagen (Biocare Medical, Walnut Creek, Calif.), and horseradish peroxidase-conjugated streptavidin (Biocare Medical). Staining with a 3,3-diaminobenzidine solution containing 0.01% hydrogen peroxide resulted in a brown color. Finally, the sections were counterstained with hematoxylin (Sigma) and observed with a microscope. Total type II and X collagen stained areas in the articular cartilage of each femur were measured using Image-Pro Plus software, version 5.0. The ratio of stained area to total area (stained: total) in each animal was calculated.

9. Modified Mankin Score

The levels of articular cartilage degeneration in the knees were evaluated and recorded using the modified Mankin score, 4 variables were included: first, surface (0=normal, 1=irregular, 2=fibrillation or vacuoles, 3=blisters or erosion); second, hypocellularity (0=normal, 1=small decrease in chondrocytes, 2=large decrease in chondrocytes, 3=no cells); third, clones (0=normal, 1=occasional duos, 3=duos or trios, 3=multiple nested cells), and fourth, alcianophilia (0=normal, 1=small decrease in color, 2=large decrease in color, 3=no color). In this evaluation system, the higher the score, the higher the level of OA. The entire histological evaluation was performed by three investigators. The investigators were blind to group allocation when this analysis was made.

Statistical Analysis

All data are expressed as mean and standard deviation (s.d.). Statistical comparisons of the histopathological grade among the control group, OA group, the OA with HA group, and the OA with HA plus MSCs group were performed with non-parametric tests, such as Wilcoxon test. Differences were considered significant when the p value was <0.05. The above tests were conducted by Statistical Package for Social Sciences (version 11.0; SPSS Inc., Chicago, Ill.).

II. Results

1. Differentiation Potential of Rabbit Bone Marrow, Hypoxia-Treated Cells

Figure 2:
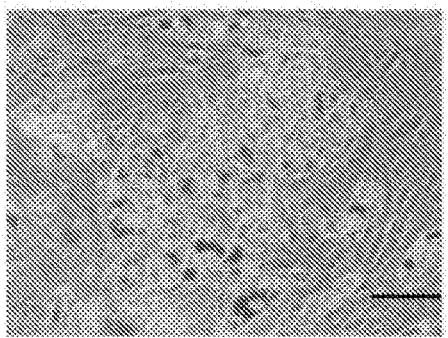
FIGS. 2A-2C show the differentiation potential of hypoxia-cultured bone marrow cells.
Figure 2:
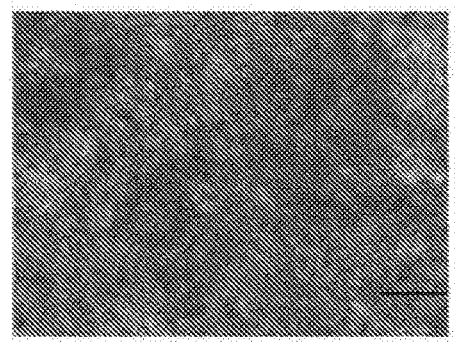
Figure 2:
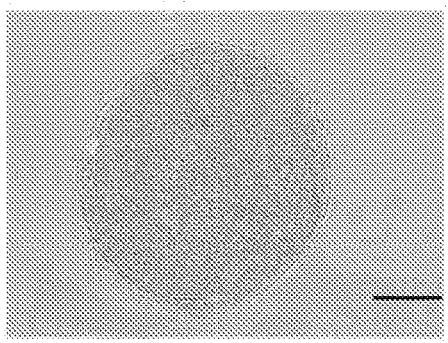

To examine whether these hypoxia-preconditioned cells have the ability of multi-potent differentiation ability, the cells were cultured in different differentiation mediums. Representative photomicrographs showed that these rabbit bone marrow cells had the ability to differentiate into adipogenic lineages, which was verified by the intracellular accumulation of Oil-Red-O-stained lipid vesicles (FIG. 2A); and osteogenic lineage, which was assayed with Alizarin Red S (FIG. 2B) and chondrogenic lineage, which was verified by Alcian-blue staining. (FIG. 2C).

2. Gross Appearance of the Femur and Tibia after Injection of the Rabbit MSCs

Figure 3:
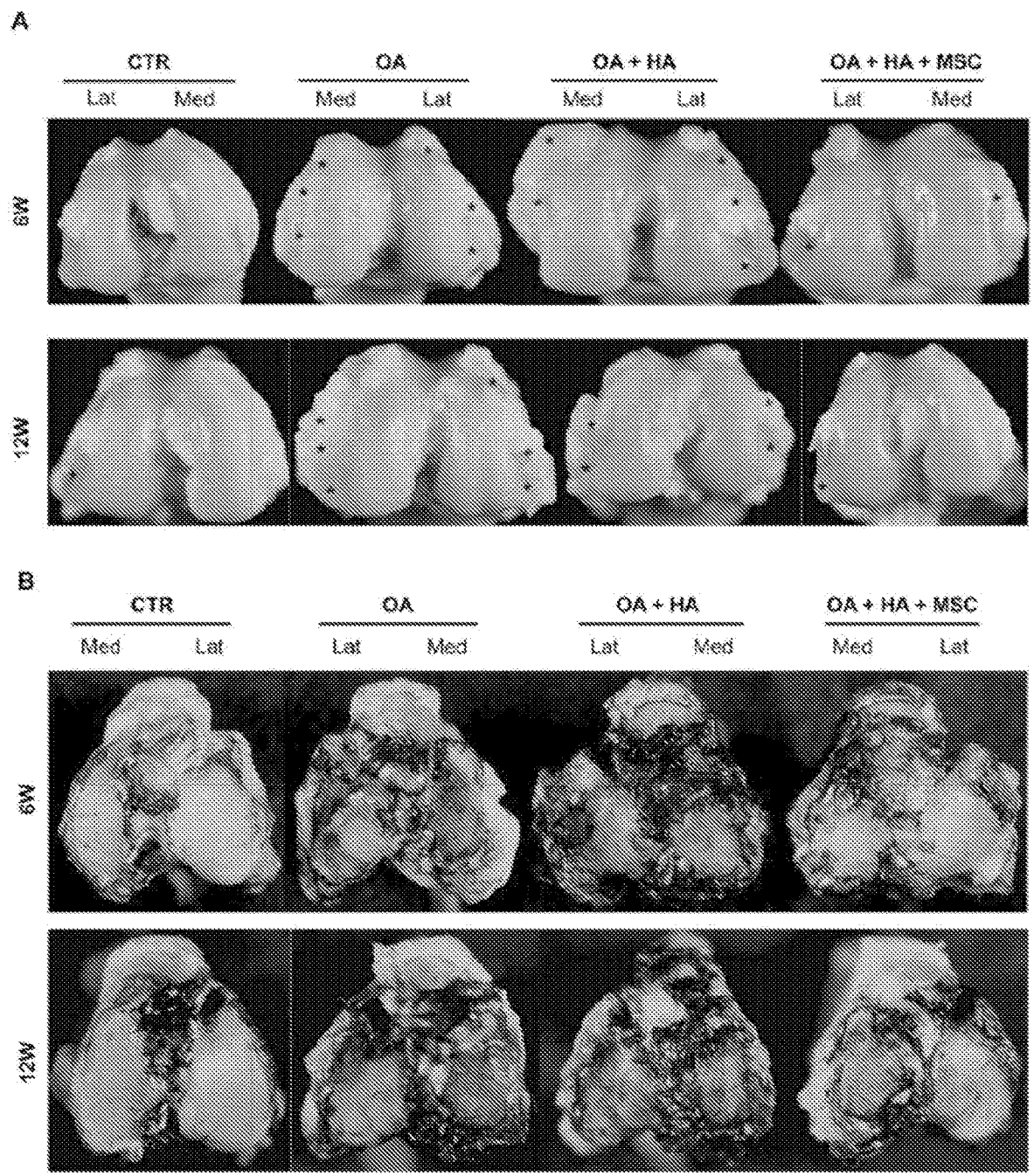
FIGS. 3A-3B show the gross appearance of the femur and tibia. The FIG. 3A shows the gross photographs of femur condyles after 6 and 12 weeks of the treatment. The asterisks of FIG. 3A indicate the formation of osteophytes.

After injection of the MSCs, the joint surface showed diminished signs of osteoarthritis, which included cartilage abrasion, osteophytes formation (asterisks), and sub-chondral bone exposure (FIG. 3A). India ink staining, which has been used to detect irregularity of articular cartilage surface, showed more fissures over tibia condyle in the groups without cell injection and these fissures were located mainly at the medial side of the joint. (FIG. 3B). These findings were both observed in 6 weeks and 12 weeks of treatment.

3. HE and Safranin O-Staining of the Femur Condyles

Figure 4:
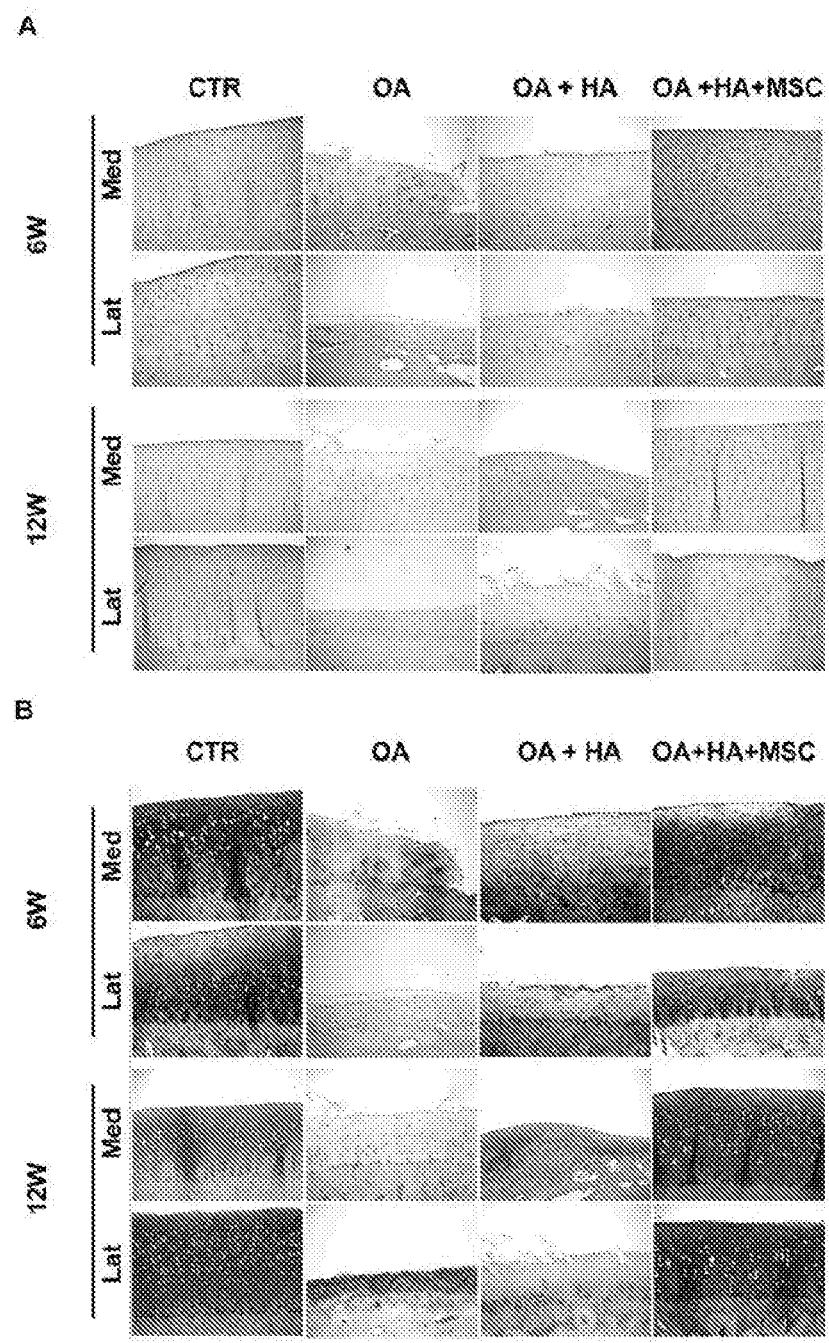
FIGS. 4A-4C show the HE and safranin-O staining of the femur condyles.

Representative photomicrographs of HE-stained articular cartilage from the OA joints and the contralateral control joints in the control studies of rabbits, as well as those from the OA treated with HA joints, and the contralateral OA treated with HA plus MSCs joints in the experimental studies of rabbits are shown in FIG. 4A. Knee joints of rabbits receiving ACLT showed surface irregularity, fibrillation or cleft, changes in cellularity, and loss of tidemark integrity, while the knee joints of the sham animal were devoid of these OA pictures (FIG. 4A). The joint surface in the group of MSCs injection showed less cartilage loss and surface irregularity as compared to OA and OA+HA group. These findings were both evident in the medial and lateral compartments of the joint (FIG. 4A).

Figure 5:
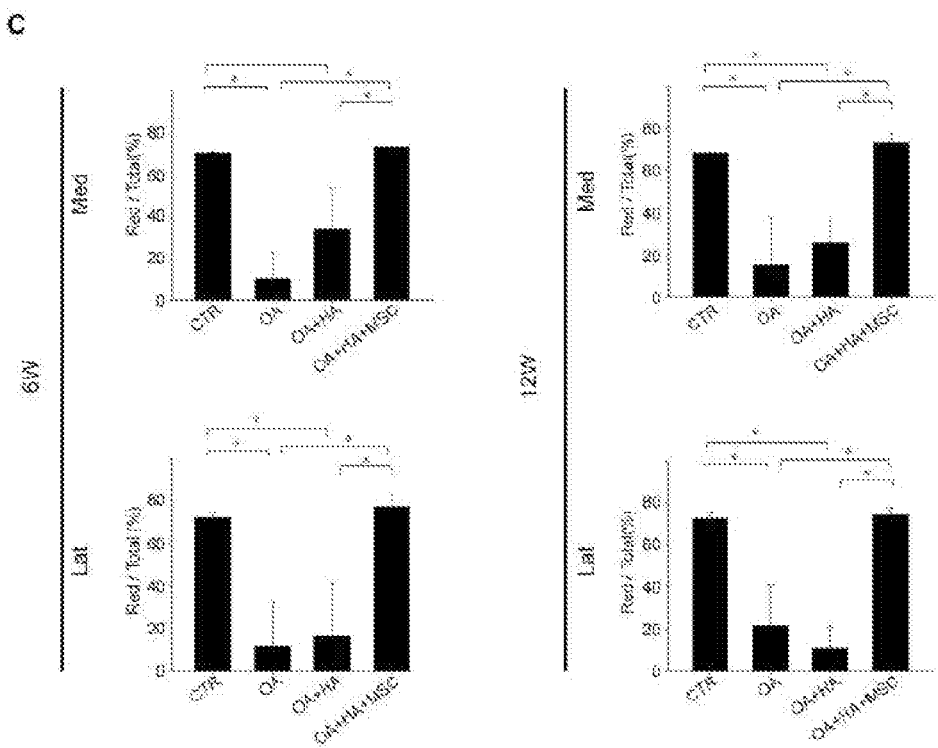
FIG. 5 shows the Mankin scores of histological grading, wherein the Mankin scores are at different part of joint after 6 and 12 weeks of the treatment. Data are presented in mean±standard deviation. *P<0.05.
Figure 5:
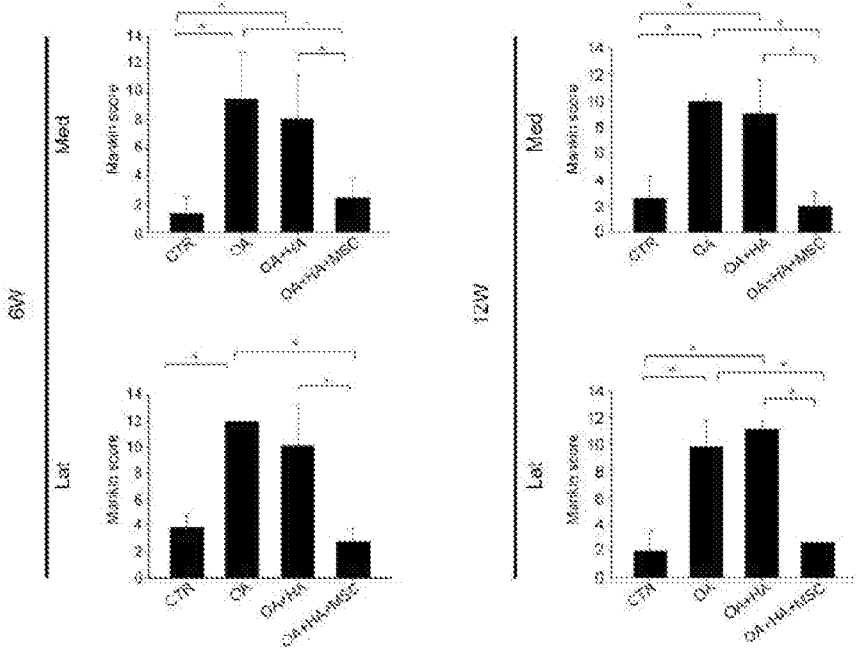

Representative photomicrographs of Safranin O-stained articular cartilage from the OA joints and the contralateral control joints in the control studies of rabbits, as well as those from the OA treated with HA joints, and the contralateral OA treated with HA plus MSCs joints in the experimental studies of rabbits are shown in FIG. 4B. The ratio of Safranin O-stained area to total area (red:total) was measured and compared among the groups (FIG. 4C). The knee joints of rabbits receiving ACLT showed reduction in Safranin O staining while the knee joints of the sham animal were devoid of these OA pictures (FIG. 4A). Safranin O staining of the cartilage showed significant loss of proteoglycan in OA and OA+HA animals (FIG. 4B). The modified Mankin score showed significant improvement after cell treatment as compared to OA and OA+HA animals. The MSC group showed comparable score to control animal. These improvements were consistent in different compartments of the joint and both in 6 weeks and 12 weeks of treatment. (FIG. 5).

4. Immunohistochemistry Staining for Type II and Type X Collagen

Figure 6:
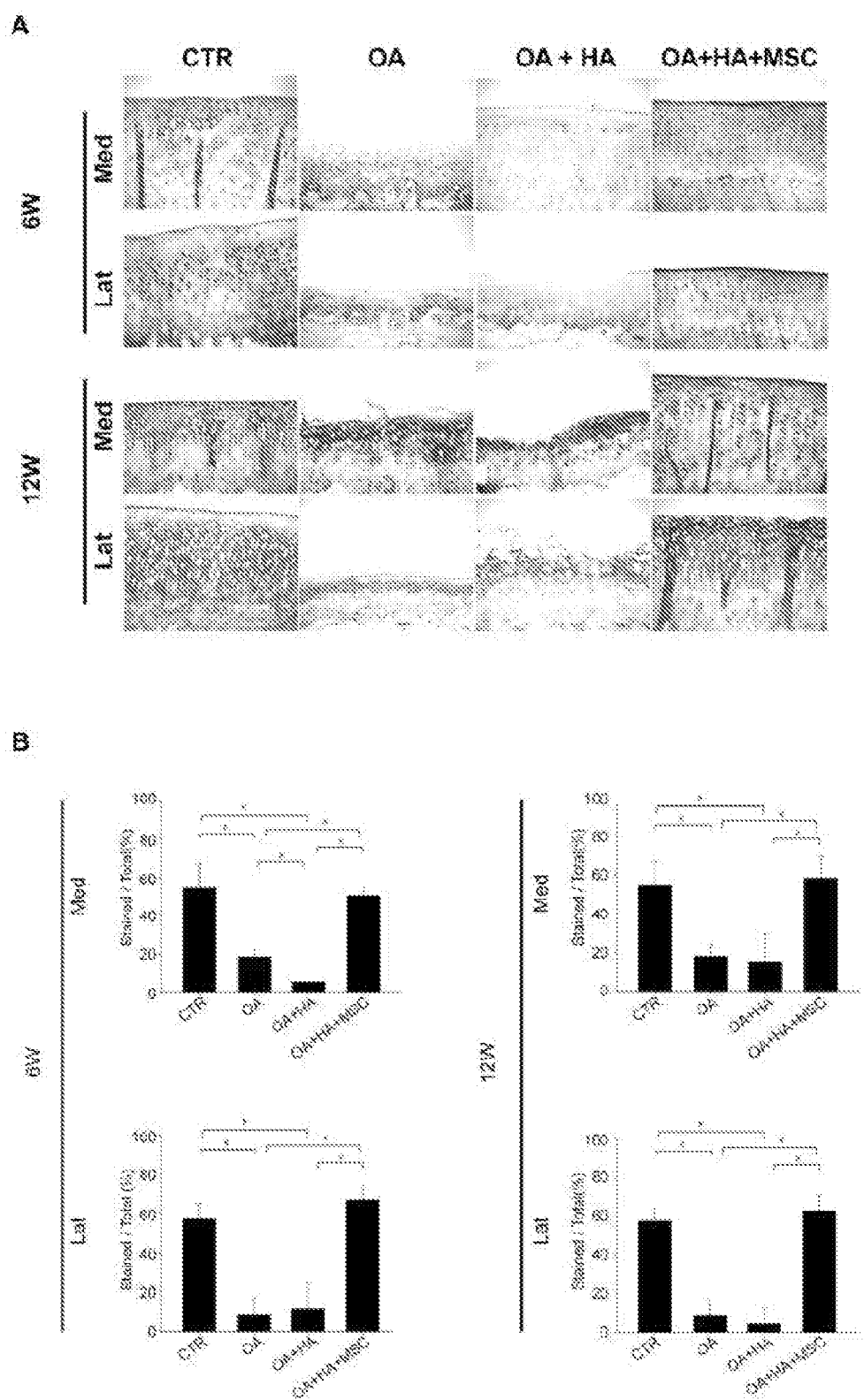
FIGS. 6A-6B show the immunohistochemistry staining for type II collagen. The FIG. 6A shows the microscopic appearance of femur condyles stained with type II collagen (Magnification, ×100). The FIG. 6B shows the quantitative analysis of type II collagen. Data are presented in mean±standard deviation. *P<0.05

Representative photomicrographs of the immunohistochemical-stained articular cartilage from the four groups are shown in FIG. 6A. Immunohistochemistry analysis by quantifying the relative density showed that the density of immunolocalized type II collagen in the OA group or OA with HA group was significantly smaller than that of MSC treated joints at both 6 and 12 weeks after MSC treatment (FIG. 6B).

Figure 7:
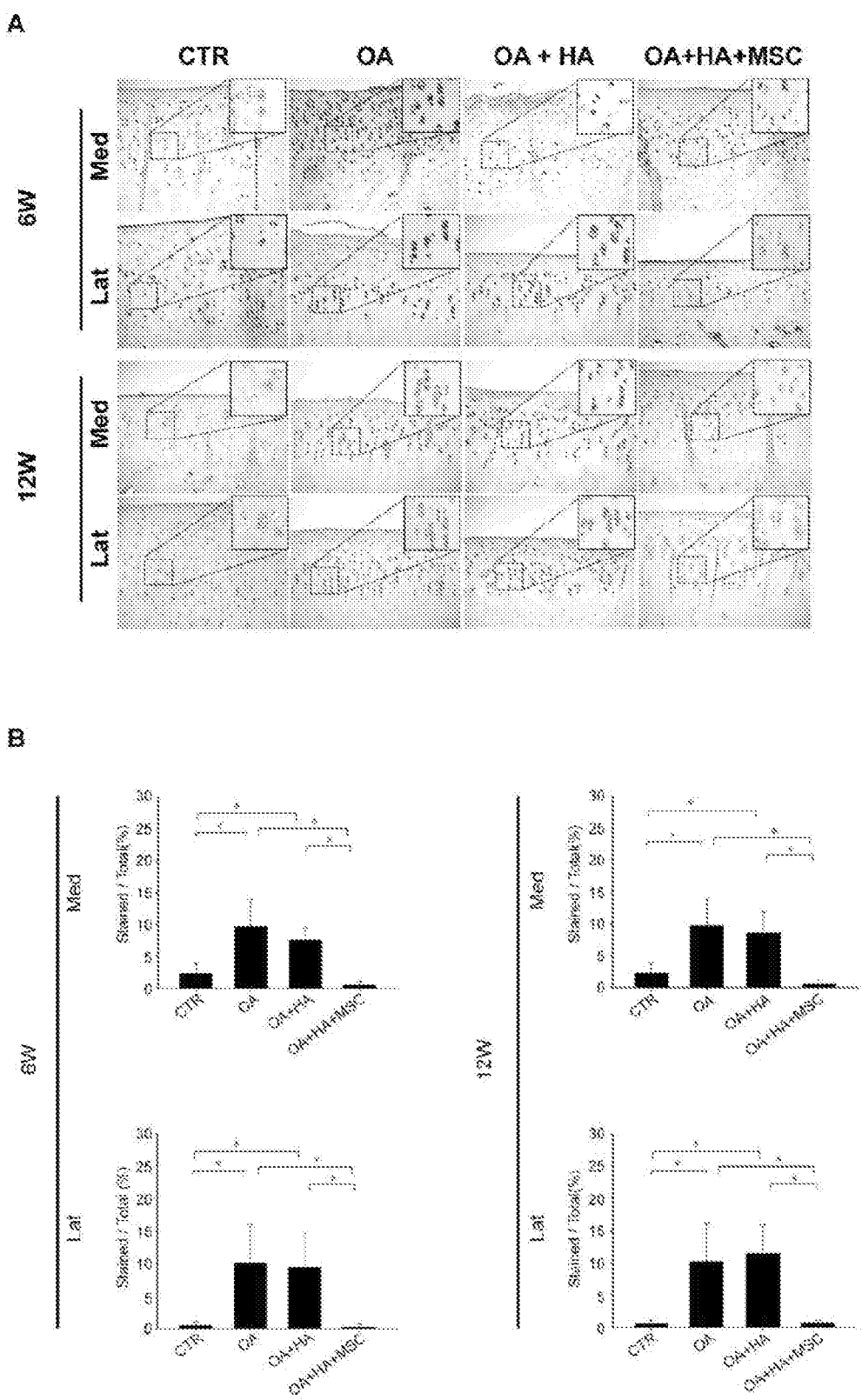
FIGS. 7A-7B show the immunohistochemistry staining for type X collagen.

Immunolocalized type X collagen (stained brown) was predominantly found in articular chondrocytes from the OA group or OA with HA group at both 6 and 12 weeks (FIG. 7A). Moreover, immunolocalized type X collagen was less evident in the cartilage of the OA treated with HA plus MSCs group compared with the OA treated with HA alone group at both 6 and 12 weeks (FIG. 7A). These data demonstrate the superior effect of HA plus MSCs in decreasing immunolocalized type X collagen compared with HA alone. A significant increase in prei-chondrocyte staining for type X collagen was also noted in OA and OA+HA groups as compared to MSC-treated group (FIG. 7B). Together, these data suggested the inhibitory effect of MSCs on the production of type X collagen.

5. Prussian Blue Stain for Hypoxic-Preconditioned and Injected MSCs

Figure 8:
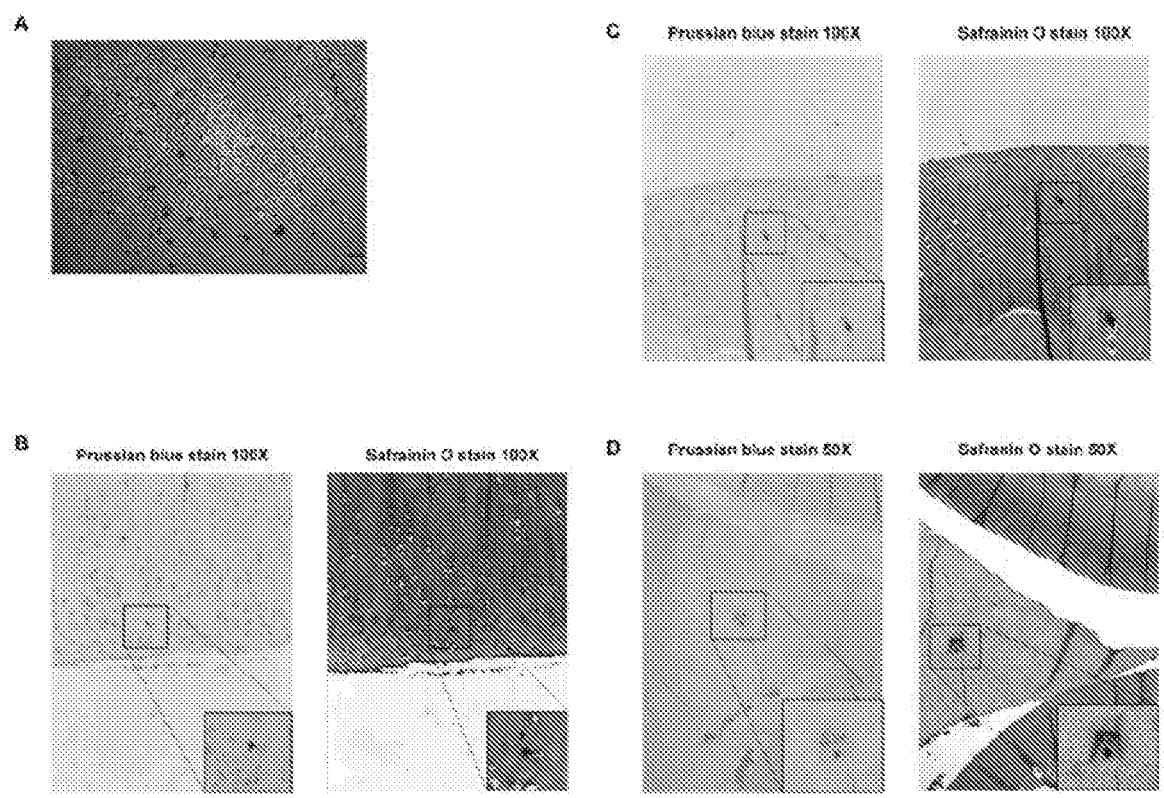
FIGS. 8A-8D show the results of Prussian blue stain for hypoxic-preconditioned and injected MSCs.

Prussian blue staining for the in vitro cell culture showed high efficiency of endocytosis of SPIO nanoparticles into the mesenchymal stem cells. (FIG. 8A) In the animals, scanty and scattered SPIO-labeled cells were identified throughout the knee joint. These injected MSCs were identified by Prussian blue staining and were located in the cartilage of femur (FIG. 8B), tibia (FIG. 8C) and meniscus (FIG. 8D). These findings suggested that SPIO-labeled cells migrated into the surface of cartilage and scattered in different part of joint after 12 weeks of injection.

It was evidenced in the above examples that the joint surface diminished the cartilage abrasion, osteophytes formation, and sub-chondral bone exposure through the administration of the composition comprising hypoxia-cultured MSCs. The loss of proteoglycan in cartilage of the subject was also improved. Besides, the production of type II collagen in cartilage of the subject was increased and the production of type X collagen in cartilage of the subject was inhibited through the administration of the composition comprising hypoxia-cultured MSCs.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A method of treating osteoarthritis, comprising:
    administering a cell culture of hypoxic mesenchymal stem cells (MSCs) to a patient in need thereof;
    wherein the cell culture are prepared by culturing MSCs in a cell medium consisting essentially of α-MEM supplemented with FBS, ascorbate-2 phosphate, dexamethasone, and β-glycerophosphate under hypoxic conditions containing oxygen in the amount ranging from 1% to 7% oxygen.

2. The method of claim 1, wherein the cell culture is administered through intra-articular injection.

3. The method of claim 2, wherein the cell culture further comprises an injectable vehicle.

4. The method of claim 3, wherein the injectable vehicle is hyaluronic acid.

5. The method claim 1, wherein the MSCs are auto- or allo-MSCs.

6. The method of claim 1, wherein the MSCs are allo-MSCs.

7. The method of claim 1, wherein the cell culture of hypoxic MSCs are obtained by culturing auto- or alto-MSCs under hypoxic conditions containing oxygen in the amount ranging from 1% to 3% oxygen.

8. The method of claim 1, wherein the cell culture of hypoxic MSCs are obtained by culturing auto- or allo-MSCs under hypoxic conditions containing oxygen in the amount of about 1% oxygen.

9. The method of claim 1, wherein the cell culture of hypoxic MSCs are obtained by the method of the steps:
   (a) preparing a mammalian cell suspension containing MSCs in culture medium;
   (b) culturing the mammalian cell suspension under hypoxic condition in culture dish, wherein said hypoxic condition is the condition containing oxygen in an amount ranging from 1% to 7% oxygen;
   (c) changing the medium and subculturing the cells under the hypoxic condition for at least 1 passage; and
   (d) recovering the MSCs as obtained in the step of (c).

10. The method of claim 9, wherein the cell culture of MSCs are cultured under the hypoxic condition for about nine days or more.

11. The method of claim 1, wherein the MSCs are bone marrow MSCs.

\* \* \* \* \*